(12) United States Patent
Schwintner et al.

(10) Patent No.: US 11,141,440 B2
(45) Date of Patent: Oct. 12, 2021

(54) PHARMACEUTICAL ORAL FORMULATION COMPRISING BACTERIA

(71) Applicants: MAAT PHARMA, Lyons (FR); BIOCODEX, Gentilly (FR)

(72) Inventors: Carole Schwintner, Lyons (FR); Marianne Robin, Lyons (FR); Jean-François Dubuisson, Lyons (FR); Hervé Affagard, Lyons (FR); Cédric Michenet, Beauvais (FR); Amandine Bardy, Beauvais (FR)

(73) Assignees: MAAT PHARMA, Lyons (FR); BIOCODEX, Gentilly (FR)

( * ) Notice: Subject to any disclaimer, the term of this patent is extended or adjusted under 35 U.S.C. 154(b) by 0 days.

(21) Appl. No.: 16/763,461

(22) PCT Filed: Nov. 16, 2018

(86) PCT No.: PCT/EP2018/081650
§ 371 (c)(1),
(2) Date: May 12, 2020

(87) PCT Pub. No.: WO2019/097030
PCT Pub. Date: May 23, 2019

(65) Prior Publication Data
US 2020/0345790 A1 Nov. 5, 2020

(30) Foreign Application Priority Data

Nov. 17, 2017 (EP) .................................. 17306602

(51) Int. Cl.
*A61K 9/48* (2006.01)
*A61K 35/74* (2015.01)
*A61K 9/00* (2006.01)
*A61K 9/19* (2006.01)

(52) U.S. Cl.
CPC ............. *A61K 35/74* (2013.01); *A61K 9/0053* (2013.01); *A61K 9/19* (2013.01); *A61K 9/4816* (2013.01); *A61K 9/4891* (2013.01)

(58) Field of Classification Search
CPC ..................................................... A61K 9/4808
See application file for complete search history.

(56) References Cited

FOREIGN PATENT DOCUMENTS

WO  2014152338 A1  9/2014

OTHER PUBLICATIONS

International Search Report and Written Opinion in PCT/EP2018/081650 dated Jan. 2, 2019.

*Primary Examiner* — Rosanne Kosson
(74) *Attorney, Agent, or Firm* — Arent Fox LLP (57) ABSTRACT

The present invention relates to a pharmaceutical oral formulation for use in the administration of at least two bacteria derived from fecal microbiota to mammals for the treatment and/or prevention of dysbiosis and associated pathologies. The pharmaceutical oral formulation is encapsulated mixture of at least two bacteria derived from fecal microbiota wherein the capsules are coated in a pH responsive polymer composition comprising:
  a. 50-70% poly(methyl acrylate-co-methyl methacrylate-co-methacrylic acid) 7:3:1 by weight of dry polymer,
  b. 10-30% poly(methacrylic acid-co-ethyl acrylate) 1:1 by weight of dry polymer,
  c. at least one fatty acid mono-, di- or tri-glyceride ester, or mixtures thereof,
  d. at least one plasticizer,
  e. at least one non-ionic emulsifier.

The pharmaceutical oral formulation is especially designed to be delivered principally in the ileum and colon and to maintain the sample bacterial viability and diversity.

20 Claims, 2 Drawing Sheets

PHARMACEUTICAL ORAL FORMULATION COMPRISING BACTERIA

TECHNICAL FIELD

The present invention relates to a pharmaceutical oral formulation for use in the administration of bacteria derived from fecal microbiota to mammals for the treatment and/or prevention of dysbiosis and associated pathologies. The pharmaceutical oral formulation may be used in autologous or allogenic fecal microbiota transplant (FMT) methods. The pharmaceutical oral formulation is advantageous compared to naso-duodenal, transcolonoscopic and enema based formulations and also compared to known FMT pharmaceutical oral formulations. The pharmaceutical oral formulation is especially designed to be delivered principally in the ileum and colon and to maintain the sample bacterial viability and diversity.

BACKGROUND OF THE INVENTION

The human intestinal microbiota is composed of all of the micro-organisms in the human gastro-intestinal system (stomach, intestine and colon). The intestinal microbiota adult individual comprises about $10^{14}$ bacteria, representing a dominant bacterial metagenome of from 200,000 to 800,000 genes per individual, i.e., 10 to 50 times the number of genes of the human genome. The intestine, which is sterile in utero, is colonized in the first days of life and evolves to a unique microbiota population. Individuals have relatively close bacterial species populations, but the exact microbiota composition (the bacterial species and their proportion) is to a great extent specific to the host. Thus, the human intestinal microbiota is a very diverse, complex ecosystem that is specific to each individual.

It is essential for the health of an individual to maintain a stable microbiota that can return to its initial state after a change and is resistant to pathogen invasion. Maintaining microbiota diversity helps provide stability. However, certain pathologies or medical treatments disrupt the microbiota, leading to dysbiosis. For example, inflammatory diseases, such as chronic intestinal inflammatory diseases can limit intestinal microbiota diversity. Iatrogenic dysbiosis occurs when the dysbiosis is caused by a medical intervention or treatment. Antibiotic treatments (or antibiotherapy), in particular, result in microbiota deterioration and loss of intestinal barrier function, which can support the proliferation of pathogenic organisms like, for example, *Clostridium difficile*, responsible for hospital-acquired diarrheas and often resistant to traditional broad spectrum antibiotics (such as vancomycin or metronidazole).

FMT is one method that is used today to restore a "healthy" intestinal microbiota. In FMT, fecal matter from a healthy donor or a group of healthy donors is introduced into the digestive tract of a patient receiver, to "reset" or cure the intestinal dysbiosis of the host. The transplantation may be allogenic (i.e., from an individual healthy donor or group of donors towards a patient) or it may be autologous, wherein fecal samples are taken from an individual before undergoing hospitalization, or antibiotic treatment, or other treatment that is likely to perturb the individual's microbiota or any event possibly generating dysbiosis.

Current methods of transplantation include naso-duodenal, transcolonoscopic or enema based methods. However, naso-duodenal administration is difficult for patients and a risk of vomiting occurs. Transcolonoscopic or enema based methods must be carried out in a hospital setting and may present discomfort for the patient and the "one-off" treatment method means that the recolonization must take place in a very limited time. Oral formulations for use in FMT represent an advantage over the latter methods from the point of view of patient comfort and convenience and are currently being developed to overcome these difficulties.

In bacterial administration methods including FMT therapy, it is important that the bacterial/microbiota sample is delivered to the ileum and colon. Therefore, an oral formulation should be able to pass intact through the stomach and be released only when it reaches the ileum or colon. The release into the neutral pH environment of the ileum and colon favors bacterial survival. Furthermore, the bacterial viability and profile (species population of the oral formulation) should be preserved.

Some reports of oral formulations for FMT are available. For example, administration of freeze-dried oral FMT formulations for the treatment of *Clostridium difficile* infection has been reported [Hecker et al. (2016) Open Forum Infect Dis (2016) 3 (2): ofw091. DOI: https://doi.org/10.1093/ofid/ofw091]. The formulation consisted of freeze dried stool suspension in size 0 capsules, each capsule containing about 60 mg of freeze dried material. The concentration of total anaerobes per ml of the freeze dried material was about $8.5*10^{10}$ CFU (Colony Forming Units)/ml, with the number of aerobic and facultative organisms at about $4.3*10^{10}$ CFU/ml to $5.0*10^{10}$ CFU/ml. It is indicated that a large number (i.e. 20-40) of capsules were ingested. This is of course unpleasant and requires a test for aspiration risk as well as the presence of a physician.

In another oral formulation, disclosed in WO 2016/201114, freeze-dried fecal microbiota is presented in a gastro-resistant size 0 capsule. The lyophilization excipient may comprise PEG 3350, glycerol, trehalose, sucrose or polyvinylpyrrolidone. The capsule head and body are banded with a low pH-resistant banding material. The capsules may be stored at approximately 4° C. It is indicated that one capsule may include approximately $6.7 \times 10^9$ CFU, and that eight capsules, taken twice a day, may be required to be equivalent to one enema dose.

In view of the increasing interest in bacterial therapy including FMT, there exists a need to provide pharmaceutical oral formulations of bacteria derived from fecal microbiota, which are effective and easy to manufacture, in particular, on an industrial scale, for use in treatment of gut dysbiosis and related pathologies. There exists a need to provide a pharmaceutical oral formulation that can deliver bacteria derived from fecal microbiota to the ileum and colon. This means that the contents of the oral formulation should not be released significantly in the gut until a pH of about 7 or greater is reached. Moreover, there exists a need to provide pharmaceutical oral formulations of bacteria derived from fecal microbiota in which the viability of the bacteria, as well as the bacterial population profile is preserved throughout the formulation manufacture as well as at the desired site of release in the gut. There exists a need to provide formulations that may be stored in the refrigerator or at room temperature and used at room temperature. There is a need to provide pharmaceutical oral formulations of bacteria derived from fecal microbiota that are stable over a long period of time.

There is a need to provide pharmaceutical oral formulations to be administered for the treatment and prevention of bacterial (iatrogenic or non-iatrogenic) gut dysbiosis and associated pathologies. The pathologies concerned may be infection, such as *Clostridium difficile*, ulcerative colitis, inflammatory bowel disease, irritable bowel syndrome, Crohn's disease, type II diabetes, food allergies, cancer, including leukemia, refractory Graft-versus-host disease (GvHD), obesity and morbid obesity. Other pathologies associated with dysbiosis are autism, sclerosis, traveller's diarrhea, chronic vaginal infection (cystitis, mycoses), bone and joint infections, intensive care unit (ICU) related dysbiosis, Parkinson's disease, Alzheimer's disease, schizophrenia and bipolar disorders and gut dysbiosis associated with anti-cancer chemotherapy or immunotherapy.

There is a need to provide pharmaceutical oral formulations to be used in treatment or prevention of iatrogenic gut dysbiosis and associated pathologies and complications including, but not limited to sepsis, septic shock and gastrointestinal disorders, including but not limited to diarrhea, mucositis, abdominal pain, gastro intestinal bleeding.

The present invention meets the above described needs.

It is therefore an object of the invention to provide a pharmaceutical oral formulation for use in FMT and for use generally in administration of at least two bacteria derived from fecal microbiota, which may be easily produced in a reliable and reproducible manner, is acceptable to the user, and which preserves the bacterial viability and diversity of the initial bacterial sample until delivery to the ileum and/or colon.

SUMMARY OF THE INVENTION

According to one aspect, the invention relates to a pharmaceutical oral formulation of an encapsulated mixture of at least two bacteria derived from fecal microbiota, wherein the capsules are coated in a pH responsive polymer composition comprising:
  a. 50-70% poly(methyl acrylate-co-methyl methacrylate-co-methacrylic acid) 7:3:1 by weight of dry polymer,
  b. 10-30% poly(methacrylic acid-co-ethyl acrylate) 1:1 by weight of dry polymer,
  c. 5 to 10% by weight of at least one fatty acid mono-, di- or tri-glyceride ester, or mixtures thereof,
  d. 5 to 8% by weight of at least one plasticizer,
  e. 6 to 9% by weight of at least one non-ionic emulsifier.

Preferably, the capsule is made from hydroxypropyl methyl cellulose.

The pH responsive polymer composition may generally comprise:
  a. 60-70% poly(methyl acrylate-co-methyl methacrylate-co-methacrylic acid) 7:3:1 by weight of dry polymer,
  b. 10-20% poly(methacrylic acid-co-ethyl acrylate) 1:1 by weight of dry polymer,
  c. 5 to 10% by weight of glycerol monostearate,
  d. 5 to 8% by weight of triethyl citrate,
  e. 6 to 9% by weight of at least one non-ionic emulsifier, preferably having a HLB between 12 and 16.

According to one embodiment of the invention, the pH responsive polymer composition may comprise:
  a. 62 to 66% poly(methyl acrylate-co-methyl methacrylate-co-methacrylic acid) 7:3:1 by weight of dry polymer,
  b. 14 to 18% poly(methacrylic acid-co-ethyl acrylate) 1:1 by weight of dry polymer,
  c. 5 to 8% by weight of glycerol monostearate (for example, 40-55),
  d. 5 to 8% by weight of triethyl citrate,
  e. 6 to 9% by weight of polysorbate 80.

According to one embodiment of the invention, the pH responsive polymer composition may comprise:
  a. 54 to 58% poly(methyl acrylate-co-methyl methacrylate-co-methacrylic acid) 7:3:1 by weight of dry polymer,
  b. 22 to 26% poly(methacrylic acid-co-ethyl acrylate) 1:1 by weight of dry polymer,
  c. 5 to 8% by weight of glycerol monostearate (for example, 40-55),
  d. 5 to 8% by weight of triethyl citrate,
  e. 6 to 9% by weight of polysorbate 80.

According to an embodiment of the invention, the pharmaceutical oral formulation may comprise an encapsulated mixture comprising the entire fecal microbiota from one or more donors.

According to an embodiment of the invention, the encapsulated mixture of at least two bacteria may be in the form of a lyophilizate.

According to an embodiment of the invention, the lyophilizate may have been produced by the following steps:
  A) Mixing a sample of fecal derived microbiota with a diluent chosen from a polyol, a di-, tri- or polysaccharide, or mixtures thereof and a filling agent, in a ratio of between 1:1 and 1:10,
  B) Freezing the mixture obtained in A) and then lyophilizing it.

According to an embodiment of the invention, the formulation comprises an entire fecal microbiota or a modified fecal microbiota of one or more donors.

According to an embodiment of the invention, the pharmaceutical oral formulation comprises a mixture of at least two bacteria derived from fecal microbiota.

According to another aspect of the invention, the pharmaceutical oral formulation may be used in autologous or allogenic fecal microbiota transplantation, or in in autologous or allogenic modified fecal microbiota transplantation.

According to another aspect of the invention, the pharmaceutical oral formulation may be used in treatment or prevention of gut dysbiosis and associated pathologies.

According to another embodiment of the invention, the associated pathologies are chosen from Clostridium difficile infection and associated diarrhea (CDI), inflammatory bowel disease (IBD), irritable bowel syndrome (IBS), idiopathic constipation, celiac disease, Crohn's disease, type II diabetes, food allergies, cancer, refractory GvHD, obesity and morbid obesity, autism, sclerosis, traveller's diarrhea, chronic vaginal infection (including cystitis, mycoses), bone and joint infections, Parkinson's disease, Alzheimer's disease, schizophrenia and bipolar disorders and gut dysbiosis associated with anti-cancer chemotherapy or immunotherapy.

According to another embodiment of the invention, the pharmaceutical oral formulation may be used in treatment or prevention of iatrogenic gut dysbiosis and associated pathologies and complications including, but not limited to sepsis, septic shock and gastro-intestinal disorders, including but not limited to diarrhea, mucositis, abdominal pain, gastro intestinal bleeding.

According to another embodiment of the invention, the pharmaceutical oral formulation may comprise the following bacteria: *Faecalibacterium prausnitzii, Bacteroides fragilis, Roseburia intestinalis, Roseburia hominis*. The latter pharmaceutical oral formulation may be used in treatment or prevention of Inflammatory Bowel Disease (IBD).

According to another embodiment of the invention, the pharmaceutical oral formulation may comprise the following bacteria: *Akkermansia muciniphila* and *Christensenella* spp.

The latter pharmaceutical oral formulation may be used in treatment or prevention of obesity and diabetes.

According to another embodiment of the invention, the pharmaceutical oral formulation may comprise the following bacteria: *Akkermansia muciniphila, Enterococcus* spp., and *Bacteroides fragilis*. The latter pharmaceutical oral formulation may be used in treatment or prevention or treatment of gut dysbiosis associated with anti-cancer chemotherapy or immunotherapy.

According to another embodiment of the invention, the mixture of at least two bacteria derived from fecal microbiota comprised in the pharmaceutical oral formulation, is substantially release at about pH 7.2, preferably at pH 7.2.

In one embodiment of the invention, the subject receiving the oral formulation is human.

DETAILED DESCRIPTION

By "pharmaceutical oral formulation" is meant a pharmaceutical oral formulation that may be used for the treatment or prevention of a pathology or physiological disorder.

By "FMT" it is meant fecal microbiota transplant, which refers to the transfer of fecal material containing microorganisms from at least one healthy donor or from at least one donor having one of more desired characteristics, into the intestinal tract of a patient. The FMT may also be autologous which means that the donor and the recipient patient are the same individual. In general, FMT refers to the complete restoration of the entire fecal microbiota.

By the term "modified FMT", is meant modified fecal microbiota transplant, which refers to FMT in which the microorganism population of the fecal material has been modified with respect to the microorganism population in the initial fecal material sample. The modification of microorganism population may be carried out by any number of methods or a combination thereof. For example, the microorganism population may be altered by culturing the fecal microorganisms in conditions that favor or disfavor the growth of certain species. This may also be referred to as microorganism selection. It may be also carried out by enrichment of the fecal microorganisms by the addition of one or more bacterial species to the fecal microorganisms. It may also be carried out by isolating a subgroup of one or more fecal microorganisms from the original fecal microorganism population. This subgroup of one or more species is then used in the modified FMT. By the term "fecal bacteriotherapy" is meant the administration of at least two bacteria derived from fecal microbiota.

By "dysbiosis" it is meant an impaired microbiota, wherein a normally dominating species becomes underrepresented, or species that are normally outcompeted or contained, are increased in population. When the dysbiosis is caused by a medical intervention, such as treatment with antibiotics or enteral feeding, it is known as iatrogenic dysbiosis.

By "therapeutically effective amount" is meant the amount required to produce the desired therapeutic effect. Generally, in the present case, a therapeutically effective amount is the bacterial load that re-establishes the desired gut colonization.

By "pH responsive polymer" is meant a polymer that dissolves at a given pH.

By "substantially released" is meant that more than 80% is released.

By "lyophilization" is meant the lyophilization or freeze-drying process. This is the removal of water from a previously frozen sample through the phases of sublimation and desorption. First, the sublimation phase, or primary drying is performed. Sublimation is when a solid (ice) changes directly to a vapor without first going through a liquid (water) phase. Then by placing the product in a deep vacuum, and rising the temperature, the solid water (ice) transforms into steam. The steam is captured in the equipment. When most of the water content of the product has been removed, the product's temperature begins to rise, indicating the end of the sublimation process. At this stage, to extract the last molecules of water, a desorption phase, or secondary drying, is performed. The desorption phase is used to remove water molecules bound to the product. To this end, the temperature is increased in the system.

Amounts are indicated as weight /volume unless otherwise indicated.

Bacterial Mixtures in the Pharmaceutical Oral Formulations:

The pharmaceutical oral formulations of the invention, in general, comprise an encapsulated lyophilized mixture comprising at least two bacteria derived from fecal microbiota, at least one cryoprotectant and, optionally, other agents.

The "at least two bacteria derived from fecal microbiota" may be an entire microbiota from an individual donor, or a pooled microbiota from a group of individual donors.

Alternatively, the "at least two bacteria derived from fecal microbiota" may be a mixture of many bacteria derived from fecal microbiota, but not the entire microbiota. The mixture may be from an individual donor, or from a group of individual donors.

For example, the mixture of many bacteria derived from fecal microbiota may be a mixture containing at least 2, or at least 5, or at least 10, or at least 20, or at least 30, or at least 40, or at least 50, or at least 60, or at least 70, or at least 80, or at least 90, or at least 100, or at least 200 or at least 300, or at least 400, or at least 500, or at least 600 or at least 700 or at least 800 or at least 900 or at least 1000 different species of bacteria.

Preferably, the mixture of many bacteria derived from fecal microbiota is a mixture containing at least two different species of bacteria.

As preferred bacteria derived from fecal microbiota for use in a mixture, we may cite the following:

*Faecalibacterium prausnitzii, Blautia hydrogenotrophica, Akkermansia muciniphila, Enterococcus* spp., *Bacteroides fragilis, Roseburia intestinalis, Roseburia hominis, Christensenella* spp., *Lactobacilles* spp.

As preferred mixtures of bacteria derived from fecal microbiota in the pharmaceutical oral formulation, we may cite the following:

*Faecalibacterium prausnitzii, Bacteroides fragilis, Roseburia intestinalis, Roseburia hominis.* This mixture may be used for the treatment of Inflammatory Bowel Desease (IBD).

*Faecalibacterium prausnitzii, Blautia hydrogenotrophica.* This mixture may be used for the treatment of irritable bowel syndrome (IBS).

*Akkermansia muciniphila, Christensenella* spp. This mixture may be used for the treatment of obesity and diabetes.

*Akkermansia muciniphila, Enterococcus* spp., and *Bacteroides fragilis.*

This mixture may be used for the treatment of intestinal dysbiosis associated with chemotherapy or immunotherapy.

The bacteria derived from fecal microbiota may be identified by 16S rRNA sequencing methods that are known to the skilled person.

Sample Preparation:

In general, the sample of the mixture of at least two bacteria derived from fecal microbiota prepared by known lyophilization techniques. Other techniques known to the skilled person may also be used. For example, one can cite microbial emulsion matrix (MEM) technology that has been developed by OpenBiome, non-profit stool bank. MEM uses long chain fatty acids to create a carrier matrix, which is a water-in-oil emulsion in which the frozen bacteria are embedded in aqueous phase micro droplets (see the "FMT Capsule G3 Clinical Primer" on www.open biome.org).

Louis et al. describe preparation of a fecal sample in pre-reduced phosphate buffer saline solution followed by serial centrifugation interspersed with decanting and resuspension of the sediments in a minimal amount of PBS. The sample is then micro injected into #1 gelatin capsules which are then over encapsulated further with #0 and #00 capsules [see Oral abstract session: new considerations in *C. difficile* prevention and treatment, fecal microbiota transplantation (FMT) via oral fecal microbial capsules for recurrent *Clostridium differential* infection (rCDI), (https://idsa.confex.com/IDSA/2013/webprogram/paper41427.html)].

Thus, the pharmaceutical oral formulation, according to an embodiment of the invention, may be prepared as described in the latter document but using suitably large, coated (with the pH responsive polymer) capsules to encapsulate suitably small gelatin capsules.

Generally, samples for use in FMT may also be prepared using the collection methods described in international patent application WO 2016/170285, which discloses methods for preparing fecal microbiota samples from donor subjects. The methods provide collecting at least one fecal microbiota sample, and placing it in an oxygen tight collection device, mixing the sample with at least one aqueous saline solution containing at least one cryoprotectant and/or filling agent, and optionally, filtering the mixture using a filter, for example, with pores of less than or equal to 0.7 mm, preferably less than 0.5 mm, and storing the mixture obtained or freezing the mixture obtained. Variants of this method, known to the skilled person, may also be used to prepare the fecal microbiota sample.

Further suitable lyophilization methods for use in sample preparation for the pharmaceutical oral formulations of the present invention are described in international patent application WO 2017/103550. For example, a sample of fecal microbiota may be prepared according to the following steps:

A) Mixing the sample of fecal microbiota from a subject donor with a diluent, for example, chosen from polyols, di-, tri or polysaccharides and a filling agent such as a maltodextrin, preferably with the ratio of fecal microbiota, preferably, purified (g)/volume of diluent (mL) comprised between 1:1 and 1:10.

B) Freezing the mixture obtained in A) at a temperature of less than −50° C., preferably at a temperature between −7° C. and −100° C., then lyophilizing the sample.

Preferably, according to one embodiment of the invention, in which the pharmaceutical oral formulation is used in FMT, the sample of fecal microbiota is a feces sample from at least one donor. Effectively, the feces sample from the donor(s) contains the fecal microbiota. In the case of autologous FMT, the donor is the subject to be treated. In the case of allogenic FMT, the donor(s) is/are not the subject to be treated.

Examples of suitable methods for collecting feces samples are described in WO 2016/170285 and in WO 2017/103550 (see pages 6 and 7).

Any suitable diluent/cryoprotectant may be used for sample preparation. Preferably, polyols or di-, tri- or polysaccharides, or a mixture thereof may be used. As a suitable polyol, one may cite glycerol, mannitol, sorbitol, propylene glycol or ethylene glycol. As suitable di-, tri- or polysaccharides, one may cite dimers, trimers, tetramers and pentamers of different or identical units, said units being chosen from glucose, fructose, galactose, fucose, and N acetylneuraminic acid. Among the suitable disaccharides that may be used, one may cite trehalose or one of its analogs or saccharose.

Preferably, the cryoprotectant is chosen from glycerol, mannitol, sorbitol, propylene glycol, ethylene glycol, trehalose and its analogs, saccharose, galactose-lactose and their mixtures. More preferably the cryoprotectant is galactose-lactose or trehalose.

Typically, the quantity of cryoprotectant present in the aqueous saline solution is comprised between 3 and 30% by weight with respect to the total volume of the solution (w/v), preferably between 4% and 20% (w/v).

As filling agents, one may cite for example, partial hydrolysates of starch, in particular, of wheat or corn, as well as partial hydrolysates of feculent, for example, potato, containing large quantities of maltodextrin. Preferably, the filling agent is a mixture of maltodextrins, in which the maltodextrin is present at between 4 and 20% (w/v).

Preferably, the diluent/cryoprotectant is an aqueous saline solution comprising at least one cryoprotectant and/or a filling agent. Thus, typically the solution contains water and physiologically acceptable salts. Typically, the solution will contain salts of calcium, sodium, potassium or magnesium with chloride, gluconate, acetate or hydrogen carbonate irons. The aqueous saline solution may optionally also contain at least one antioxidant. The antioxidant may be chosen from ascorbic acid and its salts, tocopherols, cysteine and its salts, in particular chlorhydrate, and their mixtures. Preferably, the aqueous saline solution comprises at least one salt chosen from sodium chloride, calcium chloride, magnesium chloride, potassium fluoride, sodium gluconate and sodium acetate, and optionally at least one antioxidant, preferably chosen from L-sodium ascorbate, tocopherol, L-cysteine chlorhydrate monohydrate, and mixtures thereof. Typically, the salt is present in the saline aqueous solution at a concentration of about between 5 and 20 g/L, preferably, between 7 and 10 g/L.

Typically, the antioxidant is present in the saline aqueous solution in a quantity comprised between 0.3 and 1% w/v, preferably between 0.4 and 0.6% w/v. Further details of suitable diluents/cryoprotectant may be found on page 9 of WO 2017/103550. Suitable sample lyophilization protocols are described in WO 2017/103550, on pages 10-20.

As an alternative to comprising samples of processed feces that comprise the entire gut microbiota, the pharmaceutical oral formulation, according to certain embodiments of the present invention, may comprise mixtures of least two bacteria derived from fecal microbiota. In that case, the mixture of at least two bacteria derived from fecal microbiota may be prepared according to the similar methods as those described above and detailed in WO 2017/103550. The skilled person knows how to adapt these methods to prepare a mixture of at least two bacteria derived from fecal microbiota. For example, the mixture of at least two bacteria derived from fecal microbiota may be provided as a solution or powder or other form. It may then be mixed with an aqueous saline solution comprising a cryoprotectant, and optionally a filling agent, and/or antioxidant. The mixture may then be subjected to freezing a temperature below 50° C. and then lyophilized according to the methods described in the art, in particular in WO 2017/103550.

Samples for use in modified FMT (mFMT) may be prepared in a similar way to those for FMT described above, but with additional steps to modify the fecal microorganism population. Known methods, for example, such as those described in WO 2017/103550 may be used for the isolation of the bacteria from the feces sample. The modification of fecal microorganism population may be carried out, for example, by culturing the fecal microorganisms in conditions that modify the population, for example, by favoring or disfavoring the growth of certain species. The fecal microbiota may also be modified by isolating certain bacterial species from the original fecal sample and further culturing the isolated species. The modification of the fecal microbiota may be an enrichment by the addition of one or more bacterial species to the fecal microorganisms.

Once the prepared samples of fecal microbiota, modified fecal microbiota or of at least two bacteria derived from fecal microbiota are prepared, they are then filled into capsules, using methods known to the skilled person.

Bacterial Load:

According to one embodiment of the invention, the liquid solution used for the lyophilization may contain $1*10^9$-$2*10^{10}$ bacteria per ml. Therefore, according to an embodiment of the invention, a size 0 capsule containing a lyophilized sample of this solution therefore may contain approximately $1*10^{10}$ bacteria.

A similar or identical bacterial load may be used whether the capsules contain a sample of an entire fecal microbiota or a mixture of at least two bacteria derived from fecal microbiota that is not an entire fecal microbiota.

In the latter case, where the pharmaceutical oral formulation contains a mixture of at least two bacteria derived from fecal microbiota, the liquid solution used for the lyophilization may contain $1*10^9$-$2*10^{10}$ bacteria per ml. A size 0 capsule containing a lyophilized sample of the solution, therefore, may contain approximately $1*10^{10}$ bacteria.

Capsules:

Generally, the pharmaceutical oral formulation is encapsulated in a capsule suitable for oral administration to mammals, in particular, to humans. The capsule is generally a "hard" capsule made in two halves: a lower-diameter "body" that is filled and then sealed using a higher-diameter "cap". This "hard" capsule may be made from an aqueous solution of one or more gelling agents, such as an animal protein, preferably gelatin, or a plant polysaccharide or a derivative, such as a carrageenan or modified forms of starch and cellulose. Other ingredients may be added to the gelling agent solution including plasticizers such as glycerin or sorbitol to decrease the capsule's hardness, coloring agents, preservatives, disintegrants, lubricants and surface treatment. Preferably, the capsule is made from at least one plant derived material, for example, hydroxypropyl methyl cellulose (HPMC) also known as "hypromellose", or starch hydrolysate. Suitable capsules are available from ACG (India), for example, under the commercial name "Naturecaps", or from Capsugel (New Jersey, USA) under the name "Vcaps".

Suitable capsule sizes are 5, 4, 3, 2, 2e1, 1, 0, 0e1, 00, 00e1 and 000. According to one embodiment of the invention, size 0 capsules are preferred for administration to humans.

pH Responsive Polymer:

Generally, the capsule is coated with a specific pH sensitive polymer. The pH sensitive polymer is designed so that the samples inside the capsule contents are not substantially released in the body before reaching the ileum and colon.

This means that the release should not take place below approximately pH 7.2, and the contents should release at about pH 7.2, corresponding to the pH of the ileum. Specifically, the coated capsules according to one embodiment of the invention have been designed so that, upon testing successively at pH 1.2, 6.8 and 7.2, cumulative release in the first two stages of testing is not more than 10%, preferably not more than 2%, and that more than 80% of the capsule content is released at about pH 7.2.

Dissolution tests are performed according to the United States pharmacopoeia (USP) chapter<711> and European pharmacopoeia (EP) chapter 2.9.3 using USB apparatus I, II (with a speed of 50-100 rpm) or IV. The test media temperature is adjusted to 37+/−0.5° C. One capsule is treated in a separate vessel in order to visually inspect the integrity of the capsule content at medium change or pH adjustment.

As the pH responsive polymer, the inventors have found that a composition comprising a mixture of two anionic (meth)acrylate copolymers is preferred.

The first (meth)acrylate polymer is constituted to dissolve above about pH 7.0. The second polymer is generally constituted to dissolve above about pH 5.5.

The first (meth)acrylate copolymer is generally polymerized from 10 to 30% by weight methyl methacrylate, 50 to 70% by weight methyl acrylate and 5 to 15% by weight methacrylic acid. These polymers are sold under the range name of "EUDRAGIT® FS" by Evonik (GERMANY).

Preferably, the first polymer is a copolymer polymerized from 25% by weight methyl methyl acrylate, 65% by weight methyl acrylate and 10% by weight methacrylic acid. This type of polymer is commercially available, for example, from Evonik (GERMANY) under the name of EUDRAGIT® FS. Another commercial form, under the name of EUDRAGIT® FS 30 D, which is a dispersion comprising 30% by weight EUDRAGIT® FS, is also commercially available from Evonik. The IUPAC name for the latter polymer is poly(methyl acrylate-co-methyl methacrylate-co-methacrylic acid) 7:3:1.

The second anionic (meth)acrylate copolymer is generally polymerized from 40 to 60% by weight methacrylic acid and 60 to 40% by weight ethyl acrylate. These polymers are sold under the range name of "EUDRAGIT® L" by Evonik.

Preferably, the second anionic (meth)acrylate copolymer is a copolymer polymerized from 50% by weight ethyl acrylate and 50% by weight methacrylic acid. This polymer is commercially available, for example, from Evonik under the name EUDRAGIT® L 100-55. Another commercial form, under the name of EUDRAGIT® L 30 D-55, which is a dispersion comprising 30% by weight EUDRAGIT® L 100-55, is also commercially available from Evonik. The IUPAC name for the latter polymer is poly(methacrylic acid-co-ethyl acrylate) 1:1.

Generally, the first polymer is present in the polymer composition at about 50 to 70% by weight (of dry polymer), preferably at about 55-66% of the polymer composition by weight. Generally, the second polymer is present in the polymer composition at about 10 to 30% by weight (of dry polymer), preferably at about 15 to 25%, of the polymer composition by weight.

According to a preferred embodiment of the invention, the first polymer is present in the polymer composition at about 60 to 70% by weight (of dry polymer), preferably at about 64% of the polymer composition by weight.

According to a preferred embodiment of the invention, the second polymer is present in the polymer composition at about 10 to 20% by weight (of dry polymer), preferably at about 14 to 18%, more preferably at about 16%.

According to a preferred embodiment of the invention, the first polymer is present in the polymer composition at about 54 to 58% by weight (of dry polymer), preferably at about 56% of the polymer composition by weight.

According to a preferred embodiment of the invention, the second polymer is present in the polymer composition at about 22 to 25%, preferably at about 24% of the polymer composition by weight.

According to a preferred embodiment, poly(methyl acrylate-co-methyl methacrylate-co-methacrylic acid) 7:3:1 is present in the polymer composition at 50-70% by weight of dry polymer, preferably at 55-65%, and poly(methacrylic acid-co-ethyl acrylate) 1:1 is present in the polymer composition at 10-30% by weight of dry polymer, preferably, at 22-25%.

According to a preferred embodiment, poly(methyl acrylate-co-methyl methacrylate-co-methacrylic acid) 7:3:1 is present in the polymer composition at 60-70% by weight of dry polymer, preferably at 64%, and poly(methacrylic acid-co-ethyl acrylate) 1:1 is present in the polymer composition at 10-20% by weight of dry polymer, preferably, at 14-18%, more preferably at about 16%.

According to a preferred embodiment, poly(methyl acrylate-co-methyl methacrylate-co-methacrylic acid) 7:3:1 is present in the polymer composition at 54-58% by weight of dry polymer, preferably at 56%, and poly(methacrylic acid-co-ethyl acrylate) 1:1 is present in the polymer composition at 22-25% by weight of dry polymer, preferably, at 24%.

The pH responsive polymer composition, thus, generally comprises the following components:
a. 50-70% poly(methyl acrylate-co-methyl methacrylate-co-methacrylic acid) 7:3:1 by weight of dry polymer,
b. 10-30% poly(methacrylic acid-co-ethyl acrylate) 1:1 by weight of dry polymer,
c. at least one fatty acid mono-, di- or tri-glyceride ester, or mixtures thereof,
d. at least one plasticizer,
e. at least one non-ionic emulsifier.

According to one embodiment of the invention, components a. and b. make up about 75 to 85%, preferably 80% of the pH responsive polymer composition, while components c., d. and e., make up about 25 to 15%, preferably 20% of the pH responsive polymer composition.

According to a preferred embodiment of the invention, the pH responsive polymer composition, comprises the following components:
a. 60-70% poly(methyl acrylate-co-methyl methacrylate-co-methacrylic acid) 7:3:1 by weight of dry polymer,
b. 10-20% poly(methacrylic acid-co-ethyl acrylate) 1:1 by weight of dry polymer,
c. at least one fatty acid mono-, di- or tri-glyceride ester, or mixtures thereof,
d. at least one plasticizer,
e. at least one non-ionic emulsifier.

According to another preferred embodiment of the invention, the pH responsive polymer composition, comprises the following components:
a. 55-65% poly(methyl acrylate-co-methyl methacrylate-co-methacrylic acid) 7:3:1 by weight of dry polymer,
b. 15-25% poly(methacrylic acid-co-ethyl acrylate) 1:1 by weight of dry polymer,
c. at least one fatty acid mono-, di- or tri-glyceride ester, or mixtures thereof,
d. at least one plasticizer,
e. at least one non-ionic emulsifier.

As component c., one or more known fatty acid mono-, di-or tri-esters of glycerol, suitable for use in a pharmaceutical composition, or mixtures thereof, may be used. Mono- and di-esters of glycerol are preferred. Glycerol monostearate is especially preferred for example "Glycerol monostearate 40-55".

The fatty acid ester mono-, di-or tri-glyceride may be generally present at about 5 to 10%, preferably, 6-7%, more preferably 6% of the composition by weight.

As component d., one or more known plasticizers, suitable for use in a pharmaceutical composition, may be used. As an example, one may cite triethyl citrate.

The one or more plasticizers may be generally present at about 5 to 10%, preferably, about 6-8%, more preferably, about 5-6% of the composition by weight.

Component e., one or more non-ionic emulsifiers, suitable for use in a pharmaceutical composition, known to the skilled person, are included in the polymer composition. Preferably, the non-ionic emulsifier has a HLB value of between 12 and 16. A preferred non-ionic emulsifier is polyoxyethylene (20) sorbitan monooleate (also known as polysorbate 80, and sold under the brand name Tween 80).

The one or more non-ionic emulsifier, if present, may be generally present at about 4 to 12%, preferably, about 6-10%, more preferably, about 7-9% of the composition by weight.

According to a preferred embodiment of the invention, the pH responsive polymer composition comprises:
a. 50-70% poly(methyl acrylate-co-methyl methacrylate-co-methacrylic acid) 7:3:1 by weight of dry polymer,
b. 10-30% poly (methacrylic acid-co-ethyl acrylate) 1:1 by weight of dry polymer,
c. 5 to 10% glycerol monostearate,
d. 5 to 8% triethyl citrate,
e. 6 to 9% polysorbate 80.

Components c., d., and some of component e. may be conveniently supplied as a mixture, for example under the commercial name of Plasacryl® supplied by Evonik, in Germany. According to one embodiment of the invention, if Plasacryl® is used in the manufacture of the pH responsive polymer composition, additional non-ionic emulsifier should be added to achieve the correct range for component e. For example, if the pH responsive polymer composition is comprised of 80% polymer blend components a. and b., and 20% of components c., d. and e. (at least one fatty acid mono-, di- or tri-glyceride ester, or mixtures thereof, at least one plasticizer, and at least one non-ionic emulsifier), one may add, for example, 12% Plasacryl® T20 and a further 8% of a non-ionic emulsifier to achieve the correct amounts of components c., d. and e.

According to a preferred embodiment of the invention, the pH responsive polymer composition comprises:
a. 60-70% poly(methyl acrylate-co-methyl methacrylate-co-methacrylic acid) 7:3:1 by weight of dry polymer,
b. 10-20% poly(methacrylic acid-co-ethyl acrylate) 1:1 by weight of dry polymer, c. 5 to 10% glycerol monostearate,
   d. 5 to 8% triethyl citrate,
   e. 6 to 9% polysorbate 80.

According to another preferred embodiment of the invention, the pH responsive polymer composition comprises:
   a. 50-60% poly(methyl acrylate-co-methyl methacrylate-co-methacrylic acid) 7:3:1 by weight of dry polymer,
   b. 20-30% poly(methacrylic acid-co-ethyl acrylate) 1:1 by weight of dry polymer,
   c. 5 to 10% glycerol monostearate,
   d. 5 to 8% triethyl citrate,
   e. 6 to 9% polysorbate 80.

The capsules may be coated with the pH sensitive polymer according to methods known to the skilled person. For example, one may cite drum coating or fluid bed coating. Generally, the capsules are coated with about 3.5 or 4.0 mg/cm$^2$ to about 6.0 mg/cm$^2$ of polymer applied to the capsule. As the skilled person knows, the thickness of the coating may be used to modify slightly the release time of the capsule contents. Therefore, the capsules coated with about 3.5 mg/cm$^2$ of polymer will release their contents slightly earlier in the gut than capsules coated with for example 5.5 mg/cm$^2$.

If a capsule material having a tendency to cross link with the pH responsive polymer (for example gelatin) is used, then it is recommended to carry out a pre-coating of said capsule with hydroxy propyl methylcellulose (HPMC) or methyl cellulose (HMC), preferably with 0.1-0.5 mg/cm$^2$, before proceeding with the coating with the pH responsive polymer.

If the capsules have a tendency to stick to each other or to the support or packaging material being used, after coating with the pH responsive polymer, a further coating of a cosmetic type may be employed to prevent sticking. A cosmetic coating is one which does not affect the physiological characteristics of the capsule and is typically used to change the color, texture, small or mouth feel of the oral capsule. As a cosmetic coating agent, one may cite PEG 6000, or for example Opadry® (available from Colorcon, Pa., USA).

The coated capsules may then be filled with the bacterial sample. Typically, between about 0.2 and 0.6 g, preferably about 0.4 g of dry product may be filled in a size 0 capsule.

Following filling, the capsules are closed by placing the "cap" part of the capsule on the "body" part of the capsule. The filling and closing of the capsules is carried out by methods known to the skilled person and are usually carried out in an automated or semi-automated fashion using suitable equipment. One may cite as an example a semi-manual encapsulation system like Optimatic 300 (FarmaLabor, Italy).

Alternatively, the capsules may be filled with the prepared bacterial sample and then closed, followed by coating with the pH sensitive polymer, according to methods for coating known to the skilled person.

Uses of the Pharmaceutical Oral Formulations According to the Invention:
FMT:

According to one embodiment of the invention, the pharmaceutical oral formulations are particularly suited for use in FMT.

FMT is generally used to administer one or more samples of fecal microbiota from a healthy donor, which may be an individual donor or a group of donors, to a subject suffering from dysbiosis, or at risk from developing dysbiosis and possibly also suffering from a related pathology, or at risk from developing a related pathology. Related pathologies include *Clostridium difficile* associated diarrhea (CDI), inflammatory bowel disease (IBD), irritable bowel syndrome (IBS), idiopathic constipation, celiac disease, Crohn's disease, type II diabetes, food allergies, cancer, including leukemia, refractory GvHD and morbid obesity, autism, sclerosis, traveller's diarrhea, chronic vaginal infection (including cystitis, mycoses), bone and joint infections, Parkinson's disease, Alzheimer's disease, schizophrenia and bipolar disorders.

The subject may be suffering from iatrogenic dysbiosis and related pathologies and complications including, but not limited to sepsis, septic shock, gastro-intestinal disorders (including but not limited to diarrhea, mucositis, abdominal pain, GI bleeding).

According to one embodiment of the invention, the subject is administered with a therapeutically effective amount of the pharmaceutical oral formulation.

This type of FMT is known as allogenic FMT. In the case of a group of donors, the samples of fecal microbiota are pooled and processed according to known methods thereby obtaining a fecal microbiota sample representative of the group.

According to an embodiment of the invention, the pharmaceutical oral formulations may be administered to a subject during or after a medical intervention or treatment that is likely to cause dysbiosis (iatrogenic dysbiosis).

According to one embodiment of the invention, the pharmaceutical oral formulations may be administered to a subject to prevent or treat iatrogenic dysbiosis and related pathologies and complications including, but not limited to sepsis, septic shock, gastro-intestinal disorders (including but not limited to diarrhea, mucositis, abdominal pain, GI bleeding).

If the subject himself provides a sample of fecal microbiota before the said medical intervention or treatment, and is then administered with said fecal microbiota sample, during or following the said medical intervention or treatment, the FMT is known as autologous FMT.

According to an embodiment of the invention, the pharmaceutical oral formulations may be used for administration in autologous or allogenic FMT.

According to an embodiment of the invention, the pharmaceutical oral formulations may be administered to a subject before medical treatment to increase the probability of success or efficacy of the medical treatment. For example, we may cite the area of oncology, where FMT may be carried out on patients before certain cancer treatments to increase the efficacy of the treatment (see, for example, European patent application EP 3209692. In this document, a selection of strains commonly found in healthy microbiota is used as an adjuvant to immune checkpoint blocker treatment, to immunostimulate patients, enhancing the efficacy of the treatment against cancer).

The pharmaceutical oral formulations for use in FMT generally comprise a "hard" capsule coated with a pH sensitive polymer, containing therapeutically effective amounts of a bacterial mixture. Typically, for a size 0 capsule, each capsule contains approximately $1.0*10^{10}$ to $2*10^{10}$ bacteria.

Other agents such as probiotics, prebiotics, anti-infective agents or other agents that may potentiate the gut recolonisation may also be present in the capsules.

As examples of prebiotics, we may cite 2'Fucosyllactose, Lacto-difucotetraose, 3-Fucosyllactose, Lacto-N-fucopentaose I, Lacto-N-fucopentaose II, Lacto-N-fucopentaose III, Lacto-N-neotetraose, Lacto-N-tetraose, 3'Sialyllactose, 6'Sialyllactose, 3'Sialyllacto-N-tetraose, 6'Sialyl-Lacto-N- neotetraose, inulin, fructooligosaccharide (FOS), short-chain fructooligosaccharide (short chain FOS), galacto-oligosaccharide (GOS), inulin, xylooligosaccharide (XOS), ganglioside, partially hydrolyzed guar gum, acacia gum, soybean-gum, or mixtures thereof.

As probiotics, we may cite the following *Lactobacillus paracasei, Lactobacillus rhamnosus, Bifidobacterium longum, Bifidobacterium lactis,* and *Bifidobacterium breve, Bifidobacterium animalis, Bifidobacterium infantis, Bifidobacterium adolescentis, Lactobacillus acidophilus, Lactobacillus casei, Lactobacillus salivarius, Lactobacillus lactis, Lactobacillus reuteri, Lactobacillus johnsonii, Lactobacillus plantarum, Lactococcus lactis, Streptococcus thermophilus, Enterococcusfaecium, Saccharomyces cerevisiae, Saccharomyces boulardii,* and *E. Coli Nissle.* In particular, probiotics and non-replicating probiotics, such as the genus *Lactobacillus, Bifidobacterium* or combination thereof, for example *Lactobacillus johnsonii, Lactobacillus paracasei, Lactobacillus rhamnosus, Bifidobacterium longum, Bifidobacterium lactis, Bifidobacterium breve,* or combinations thereof, and/or non-viable fractions of these bacteria.

As examples of anti-infective agents, we may cite bactericide agents such as reuterin, lactococcins or specific phages.

As examples of other agents that may potentiate the gut recolonisation, we may cite micro-nutriments as for example zinc or copper, or polyphenols.

Modified FMT:

According to one embodiment of the invention, the pharmaceutical oral formulations are particularly suited for use in modified FMT (mFMT). mFMT may be used to administer one or more samples of modified fecal microbiota from a healthy donor, which may be an individual donor or a group of donors, to a subject. The subject may be suffering from dysbiosis, or at risk from developing dysbiosis and possibly also suffering from a related pathology, or at risk from developing a related pathology. Related pathologies include *Clostridium difficile* associated diarrhea (CDI), inflammatory bowel disease (IBD), irritable bowel syndrome (IBS), idiopathic constipation, celiac disease, Crohn's disease, type II diabetes, food allergies, cancer, refractory GvHD and morbid obesity, autism, sclerosis, traveller's diarrhea, chronic vaginal infection (including cystitis, mycoses), bone and joint infections, Parkinson's disease, Alzheimer's disease, schizophrenia and bipolar disorders. mFMT can be used to ensure the therapeutically effective of a specific bacterium or mixture of specific bacteria in the pharmaceutical formulation. Generally, the amount of the bacteria to be delivered to the gut is such that the final relative population of that delivered bacteria or mixture of bacteria is significantly increased with respect to the population before mFMT. For example, it is desired that a therapeutically effective amount of *Faecalibacterium prausnitzii* is delivered to the gut in the treatment or prevention of inflammatory bowel diseases. The amount to produce the therapeutic effect depends on the relative abundance of *Faecalibacterium prausnitzii* in the gut. In this case, the oral formulation should contain enough bacterial to increase this relative abundance of *Faecalibacterium prausnitzii* in the gut, at least to 15%. The skilled person knows how to dose the bacterium or mix of bacteria so that the colonization target is reached.

The subject may be scheduled to undergo a medical intervention. The modification of fecal microbiota may be carried out, for example, by culturing the fecal microorganisms in conditions that favor or disfavor the growth certain species. This may also be referred to as microorganism selection. It may be also carried out by enrichment of the fecal microorganisms by the addition of one or more bacterial species to the fecal microorganisms. It may be also carried out by isolating a subgroup of one or more fecal microorganisms from the original fecal microorganism population. This subgroup of one or more species is then used in the modified FMT. Typically, in the oral formulations for use in mFMT, for a size 0 capsule, each capsule contains approximately $1.0*10^{10}$ to $2*10^{10}$ bacteria.

Fecal Bacteriotherapy:

According to one embodiment of the invention, the pharmaceutical oral formulations are particularly suited for use in fecal bacteriotherapy. According to this embodiment, the administered capsules comprise a mixture of at least two bacteria derived from fecal microbiota for the treatment or prevention of pathologies associated with dysbiosis.

The subject is administered with a therapeutically effective amount of the pharmaceutical oral formulation.

Preferably, the complex mixture of many bacteria derived from fecal microbiota is a mixture containing at least two different species of bacteria.

As mixtures of bacteria derived from fecal microbiota, we may cite mixtures chosen from the following bacteria: *Faecalibacterium prausnitzii, Blautia hydrogenotrophica, Akkermansia muciniphila, Enterococcus* spp., *Bacteroides fragilis, Roseburia intestinalis, Roseburia hominis, Christensenella* spp., *Lactobacilles* spp.

For example, the pharmaceutical oral formulation according to one embodiment of the invention comprises a mixture of the following bacteria *Faecalibacterium prausnitzii, Bacteroides fragilis, Roseburia intestinalis, Roseburia hominis.* This mixture may be used for the treatment of Inflammatory Bowel Desease (IBD).

According to one embodiment of the invention, the pharmaceutical oral formulation comprises a mixture of the following bacteria *Akkermansia muciniphila, Christensenella* spp. This mixture may be used for the treatment of obesity and diabetes.

According to another embodiment of the invention, the pharmaceutical oral formulation comprises a mixture of the following bacteria *Akkermansia muciniphila, Enterococcus* spp., and *Bacteroides fragilis.* This mixture may be used for the treatment of intestinal dysbiosis associated with chemotherapy or immunotherapy.

As was the case for the pharmaceutical oral formulations for use in FMT, in which an entire fecal microbiota is transplanted, the pharmaceutical oral formulations for use in "fecal bacteriotherapy" in which mixtures of at least two bacteria derived from fecal microbiota are administered, comprise a "hard" capsule coated with a pH sensitive polymer, containing therapeutically effective amounts of a bacterial mixture. Typically, for a size 0 capsule, each capsule contains approximately $1.0*10^{10}$ to $2*10^{10}$ bacteria. As was discussed for mFMT, the amount of bacteria or mixture of bacteria to be delivered to the gut is generally an amount such that the final relative population of that bacteria or mixture of bacteria is increased with respect to the relative population before the fecal bacteriotherapy. The skilled person knows how to dose the bacterium or mixture of bacteria so that the colonization target is reached.

Other agents such as prebiotics, anti-infective agents or other agents including probiotics, that may potentiate the gut recolonisation, may also be present in the capsules.

As probiotics, we may cite the following *Lactobacillus paracasei, Lactobacillus rhamnosus, Bifidobacterium longum, Bifidobacterium lactis,* and *Bifidobacterium breve, Bifidobacterium animalis, Bifidobacterium infantis, Bifido-*

*bacterium adolescentis, Lactobacillus acidophilus, Lactobacillus casei, Lactobacillus salivarius, Lactobacillus lactis, Lactobacillus reuteri, Lactobacillus johnsonii, Lactobacillus plantarum, Lactococcus lactis, Streptococcus thermophilus, Enterococcusfaecium, Saccharomyces cerevisiae, Saccharomyces boulardii,* and *E. Coli Nissle.* In particular, probiotics and non-replicating probiotics, such as the genus *Lactobacillus, Bifidobacterium* or combination thereof, for example *Lactobacillus johnsonii, Lactobacillus paracasei, Lactobacillus rhamnosus, Bifidobacterium longum, Bifidobacterium lactis, Bifidobacterium breve,* or combinations thereof, and/or non-viable fractions of these bacteria.

As examples of anti-infective agents, we may cite bactericide agents such as reuterin, lactococcins or specific phages.

As examples of other agents that may potentiate the gut recolonisation, we may cite micro-nutriments as, for example, zinc or copper, or polyphenols.

Advantages and Efficacy of the Pharmaceutical Oral Formulations:

The pharmaceutical oral formulations of the invention provide an efficacious, reliable, easy to use dosage form for FMT therapy and also for fecal bacteriotherapy. The oral formulations of the invention are especially suitable for FMT therapy as they deliver their contents in the ileum and colon. The formulations thus have excellent dissolution profiles, with no significant content release between pH 1.2 and pH 6.8, followed by rapid release at pH 7.2.

The precision achieved with respect to content release at pH 7.2 or above, is due to the pH sensitive polymer mixture used to coat the capsules. Without being bound by theory, it is considered that exact quantities of components c., d. and e. serve to efficiently homogenize the polymer mixture of components a. and b., thereby providing an extremely homogenous coating and allowing rapid release initiation at pH 7.2. As detailed above, the relative proportion of each of the polymer components a. and b. is important, as well as the proportion of the mixture of a. and b. to the proportion of c., d. and e. generally the proportion of [a.+b.]:[c.+d.+e.] is 75-85: 15-25, 80:20. Surprisingly, the inventors have also found that the claimed quantities (6-9%) of non-ionic surfactant (component e.) are particularly important to achieve release initiation at a pH of 7.2 and, thus, without significant release at pH 6.8. Lower proportions of non-ionic surfactant do not allow delivery to begin in the ileum and colon, because release initiation is at a pH lower than 6.8 (data not shown).

Relatively efficacious doses of bacteria for gut recolonization may be included in the pharmaceutical oral formulations, thereby reducing the number of capsules that have to be ingested by the patient. This represents a significant advantage over other methods of bacteriotherapy and FMT, and even with respect to other pharmaceutical oral formulations for bacterial mixtures Typically, the bacterial load in an FMT enema is about $5*10^{10}$ to $6*10^{10}$ bacteria, a suitable amount for good recolonisation. According to one embodiment of the invention, one capsule of the pharmaceutical oral formulation may contain from $1.0*10^{10}$ to $2*10^{10}$ bacteria. Therefore, administration of four or five capsules to a subject may be sufficient to provide a sufficient bacterial load so that gut recolonisation with the fecal microbiota of the pharmaceutical oral formulation occurs.

One important advantage of the pharmaceutical oral formulations is that they may be ingested by the subject without medical surveillance. They do not need to be frozen and may be stored in the refrigerator or at room temperature. These advantages lead to greater patient comfort and compliance. This also means that the treatment may be taken over a number of days if necessary, thereby, allowing the gut recolonisation to occur progressively. Therefore, the treatment may be taken over a period of several, for example 3, 4, 5 or 6 days, compared to 1 or 2 days that are habitual for enema or transcolonic treatments.

The advantage of the use of the pharmaceutical oral formulations of the invention is that the mixture of bacteria derived from fecal microbiota is delivered to the ileum and colon, without having been released in the stomach or duodenum. The bacterial viability is conserved and the taxonomic (diversity) profile preserved. Example 3 describes a set of dissolution tests on capsules according to Example 2. The capsules of Example 2 containing caffeine underwent USP2 Dissolution tests as well as adapted USP2 dissolution tests. The USP2 Dissolution test results are shown in Table 2 and FIG. 1*a*. The results indicate that there is no significant dissolution at pH 1.2 and pH 6.8. The release starts rapidly at pH 7.2.

Similarly, in the adapted USP 2 dissolution tests which discriminate more specifically the jejunum (pH 6.8) and the ileum (pH 7.2), it is noted that there is no significant (less than 1%) release at pH 1.2 and pH 6.8. However, release is rapid at pH 7.2. The adapted USP2 dissolution test results are shown in Table 3 below.

Figure 2:
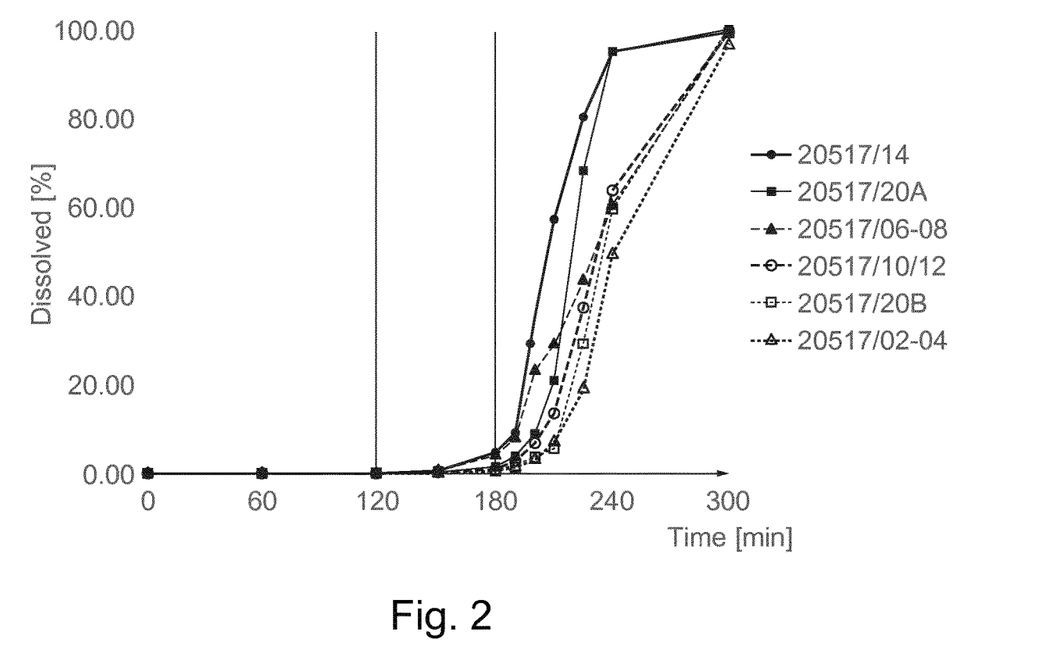
FIG. 2 is a dissolution profile obtained for a number of pharmaceutical oral formulations according embodiments of the invention using the USP2 method.

A number of batches of capsules according to the different embodiments of the invention were manufactured (see Example 4 below) and tested in the USP2 dissolution tests (See Example 5). All batches consisted of capsules that were coated with the EUDRAGIT® polymer blend, EUDRAGIT® FS 30 D/EUDRAGIT® L 30 D-55. Some of the batches were additionally coated with PEG 6000 to prevent the capsules from sticking to each other. The dissolution profiles obtained in Example 5 are shown in FIG. 2. The results indicate that there is no significant dissolution at pH 1.2 and pH 6.8. The release starts rapidly at pH 7.2.

We note that Batch #14 corresponds to a capsule coated with 3.5 mg/cm² of the EUDRAGIT® polymer blend, while Batch #20B corresponds to a capsule coated with 5.5 mg/cm² of the EUDRAGIT® polymer blend. Both batches are coated using drum coating. We note that Batch #20B releases its content slightly later (about 30 minutes) than Batch #14.

Further dissolution tests were carried out in a TIM-1 system which is a preclinical model of the gastrointestinal tract composed of four compartments, i.e. the stomach, the duodenum, the jejunum and the ileum. In this test, release occurs only in the ileum.

The conservation of bacterial viability and preservation of the microbiota diversity has also been demonstrated by the applicant for the pharmaceutical oral formulations, according to an embodiment of the invention. Example 1 describes a freeze-dried FMT product preparation, in which stool was collected and a sample of freeze-dried fecal microbiota was prepared. The taxonomic profile of the sample was estimated using targeted (16S) meta-genomics data obtained by sequencing the V3-V4 segment of the 16S rDNA gene using standard methods. The profiling was carried out before and after freeze-drying and intermediate storage, as well as before and after milling and encapsulation. The formulations were found to have preserved viability as well as preserved diversity.

The invention is further described with reference to the following examples. It will be appreciated that the invention as claimed is not intended to be limited in any way by these examples.

EXAMPLE 1

Freeze-Dried FMT Product Preparation

1) Stool Collection and Inoculum Preparation

Fresh stool was collected in a suitable device (for maximum of 72 hours) and the sample was transformed into a liquid inoculum using the method disclosed in Example 2 of international patent application WO 2017/103550. The bacterial viability of the inoculum before freeze drying was determined using cell flow cytometry technology in the standard way. The inoculum taxonomic profile was estimated using targeted (16S) metagenomics data obtained by sequencing the V3-V4 segment of 16S rDNA gene, using standard methods.

2) Freeze-Drying and Intermediate Storage

The inoculum was freeze dried according to the method described in Example 3 of WO 2017/103550. After freeze-drying, the lyophilizates were manually crushed and stored in protective packaging (PE/glass tubes with desiccant stopper or aluminum pocket with zipper). The lyophilizate viability was determined and its taxonomic profile estimated.

3) Milling and Encapsulation

After storage, the products were milled using a knife-miller (Tube Mill—single-use capsules, IKA Werke GmBH &Co. KG, Germany), with milling performed between 10,000 and 5000 RPM, for 20 to 40 seconds. The milled lyophilizate viability was determined and its taxonomic profile estimated.

The formulations were found to provide a quantity of viable bacteria ranging from $6.80*10^9$ to $1.39*10^{10}$ unit/0.5 grams of milled product.

Preservation of microbiota diversity was confirmed by calculating the Alpha-diversity indexes richness and Simpson's index for each sample. Richness is the number of different species (OTU) observed within a sample. Simpson's index is derived from the richness and considers the relative abundance of each species, it is comprised between 0 and 1 (0, mostly one dominant species→1, mostly many rare species or several dominant and many rare species). Within each pair (an inoculum and its derived lyophilizate), the richness gave a value of between 225 and 325 species. The maximal difference within a pair was approximatively 25 species, which is very limited. The Simpson index reduction between inoculum and lyophilizate ranged between 1 and 2%. This means that the richness of the samples is maintained after freeze drying and lyophilization.

Furthermore, the sample microbiota profiles were strongly conserved between inoculum and lyophilizate. All Bray-Curtis similarity ranged between 0.89 and 0.92.

Lastly, the products were encapsulated in the capsules according to Example 2 using a semi-manual encapsulation system like Optimatic 300 (Farmalabor, ITALY). Filled capsules were placed in protective packaging (PE/glass tubes with desiccant stopper or aluminum pocket with zipper, or blister).

EXAMPLE 2

Capsule coating

Size 0 hypromellose capsules are coated in a pH responsive polymer.

The polymer composition is described in Table 1.

TABLE 1

| pH-responsive polymer composition | | |
|---|---|---|
| Component | General Ratio | Preferred Ratio |
| EUDRAGIT ® FS 30 D (dry polymer) | 60-70% | 62-66% |
| EUDRAGIT ® L 30 D-55 (dry polymer) | 14-18% | 15-16% |
| Glycerol monostearate 40-55 | 4-8% | 5-7% |
| Triethyl citrate | 4-8% | 5-6% |
| Polysorbate 80 (Tween ® 80) | 6-10% | 7-9% |

The components are mixed together and the polymer is filtered (250 um).

The capsule head and body are coated separately using air fluidized bed equipment (Glatt GPCG-5), by either bottom spraying, or top spray, or tangential spraying. The equipment is generally operated under the following conditions:

Air flow rate: 250 to 350 m³/h
Air flow temperature: 35 to 40° C.
Product temperature: 25 to 28° C.
Spraying velocity: 15 to 25 g/min
Polymer applied: 4.0 to 6.0 mg/cm²

EXAMPLE 3

Dissolution Tests on Caffeine Filled Capsules of Example 2

The dissolution profiles of hypromellose capsules that were coated according to Example 2 and filled with caffeine were determined.

(a) USP 2 Dissolution Tests

Three capsules were exposed to pH 1.2 for 2 hours, then, pH 6.8 for 1 hour and finally, pH 7.2, for 2 hours. USP 2 dissolution tests were performed using ERWEKA DT 700 Paddle Apparatus, set at 37° C. and 75 RPM. At each time-point, capsule deterioration was determined using caffeine detection in the medium with HPLC-UV. HPLC-UV was performed on 10 µL of the medium, on an Agilent 1100er series using the following run parameters:

Column: Gemini 2 µm C18 100 mm×4.6 mm
Mobile phase: mix of Methanol Licrosolv and Purified water (3/7 ratio)
Flow rate: 1 mL/min
Runtime: 8 minutes
Detector wavelength: 273 nm The results are shown in Table 2 and in FIG. 1a:

TABLE 2

| Results of dissolution profile according to USP 2 method | | | | |
|---|---|---|---|---|
| Medium | Time [min] | Capsule 1 | Capsule 2 | Capsule 3 |
| pH 1.2 | 0 | 0.07 | 0.00 | 0.00 |
| pH 1.2 | 60 | 0.00 | 0.00 | 0.06 |
| pH 1.2 | 120 | 0.00 | 0.00 | 0.06 |
| pH 6.8 | 150 | 0.00 | 0.00 | 0.22 |

TABLE 2-continued

Results of dissolution profile
according to USP 2 method

| Medium | Time [min] | Capsule 1 | Capsule 2 | Capsule 3 |
|---|---|---|---|---|
| pH 6.8 | 180 | 0.04 | 0.10 | 1.07 |
| pH 7.2 | 190 | 0.53 | 0.38 | 48.22 |
| pH 7.2 | 200 | 97.40 | 86.45 | 69.18 |
| pH 7.2 | 210 | 99.35 | 97.33 | 98.81 |
| pH 7.2 | 225 | 99.89 | 100.07 | 99.89 |
| pH 7.2 | 240 | 99.97 | 99.99 | 100.09 |
| pH 7.2 | 300 | 99.99 | 99.88 | 100.19 |

Figure 1A:
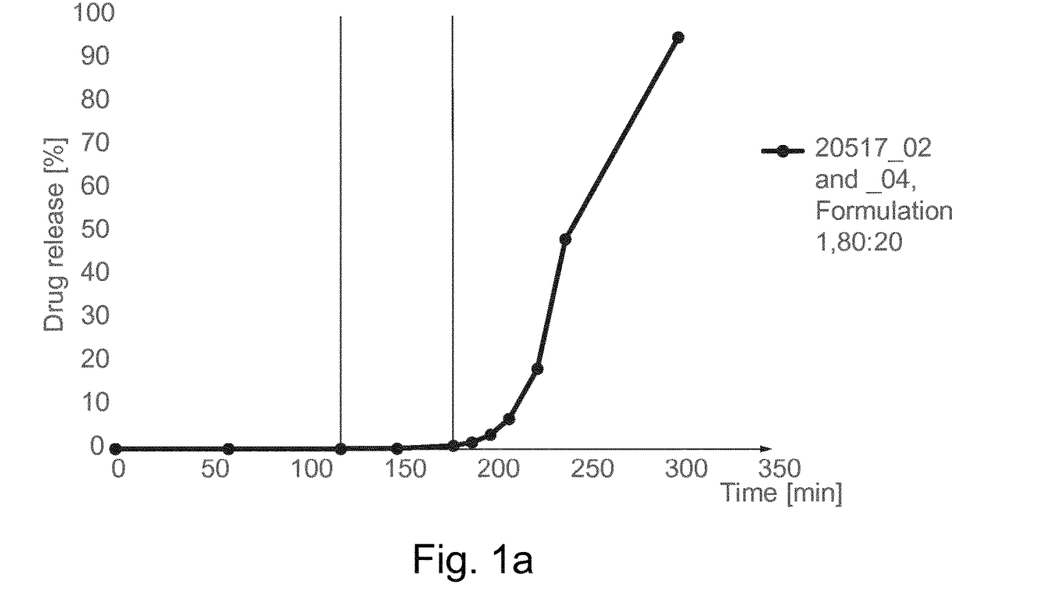
FIG. 1*a* is a dissolution profile obtained for a pharmaceutical oral formulation according to one embodiment of the invention using the USP2 method.

FIG. 1a shows the profile of capsule dissolution for USP 2 method. No significant (<1%) dissolution is observed at pH 1.2 and 6.8. The release starts rapidly at pH 7.2.

(b) Adapted USP 2 dissolution tests: The adapted USP 2 method discriminates more specifically the jejunum (pH 6.8) and the ileum (pH 7.2).

Adapted USP 2 dissolution tests were performed using ERWEKA DT 700 Paddle Apparatus, set at 37° C. and 75 RPM. Capsules were exposed to HCl solution 0.1N pH 1.2 (fasted stomach) for 2 hours, then phosphate buffer pH 6.8 (jejunum) for 1 hour and finally phosphate buffer pH 7.2 (ileum) for 2 hours. At each time-point, capsule deterioration was determined using caffeine detection in the medium with HPLC-UV.

HPLC-UV chromatography was performed on 10 μL of the medium, on an Agilent 1100er series using the following run parameters:

Column: Gemini 2 μm C18 100 mm×4.6 mm
Mobile phase: mix of Methanol Licrosolv and Purified water (3/7 ratio)
Flow rate: 1 mL/min
Runtime: 8 minutes
Detector wavelength: 273 nm

TABLE 3

Dissolution profile with
USP 2 adapted method

| Medium | Time [min] | Capsule 1 | Capsule 2 | Capsule 3 |
|---|---|---|---|---|
| pH 1.2 | 0 | 0.09 | 0.00 | 0.00 |
| pH 1.2 | 60 | 0.08 | 0.00 | 0.53 |
| pH 1.2 | 120 | 0.13 | 0.00 | 0.00 |
| pH 6.8 | 150 | 0.21 | 0.00 | 0.00 |
| pH 6.8 | 180 | 0.44 | 0.13 | 0.00 |
| pH 7.2 | 190 | 0.90 | 0.45 | 0.00 |
| pH 7.2 | 200 | 4.45 | 1.47 | 0.00 |
| pH 7.2 | 210 | 10.17 | 4.51 | 1.92 |
| pH 7.2 | 225 | 27.79 | 74.12 | 25.11 |
| pH 7.2 | 240 | 68.37 | 99.07 | 47.44 |
| pH 7.2 | 300 | 100.65 | 99.31 | 99.53 |

Figure 1B:
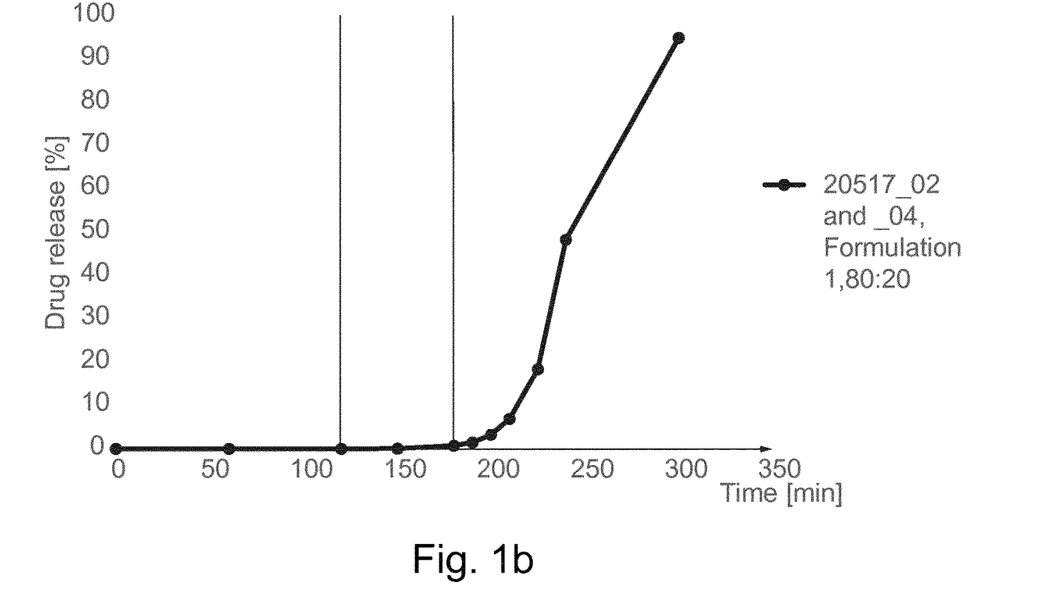
FIG. 1*b* is a dissolution profile obtained for a pharmaceutical oral formulation according to one embodiment of the invention using the adapted USP2 method.

Table 3 and FIG. 1b show the profile of capsule dissolution for an adapted USP2 test.

The profile demonstrates the ileo-colic delivery functionality, with no significant (<1%) dissolution at pH 1.2 and 6.8. Release is rapid at pH 7.2.

(c) TIM

TIM-1 system is a pre-clinical equipment mimicking the gastro-intestinal tract. It is composed of 4 compartments, i.e., the stomach and the duodenum, jejunum, and ileum.

Each compartment is composed of glass units with a flexible inner membrane, and filled with medium at relevant pH. Four assays were launched on TIM-1 system: MP01 (Assay 1), MP02, MP03 (Assay 2) and MP04 (Assay 3).

MP02 was discontinued due to leakage in the TIM operating system.

For Assay 1 (MP01): Visual observation and plate count confirms stomach resistance. Release starts at the very end of the jejunum and is confirmed in the ileum despite the absence of visual observation of a clear dissolution.

For Assay 2 (MP03): Visual observation and plate count confirms the targeted functionality, dissolution is detected in ileum.

For Assay 3 (MP04): Visual observation and plate count confirms the targeted functionality, dissolution is detected in ileum.

As shown by the USP2, adapted USP2 and the TIM experiments, the functionality of the capsule is confirmed.

The experiments show that, for all the capsules, the release will start at the end of the jejunum, and would be either completed by the end of the jejunum or continue in the colon, even if the pH decreases.

For all open capsules, the delivery was not total at the end of the jejunum, nonetheless, once the capsule is open, the delivery can continue throughout the colon even if the pH decreases.

EXAMPLE 4

A Number of Capsule Batches were Manufactured

Size 0 hypromellose capsules are coated in a pH responsive polymer. The polymer composition is described in Table 4a. The polymer blend ratio used and coating conditions are described in Table 4b.

TABLE 4a pH-responsive polymer composition

| Component | General Ratio | Preferred Ratio |
|---|---|---|
| EUDRAGIT ® FS 30 D (dry polymer) | 50-70% | 55-65% |
| EUDRAGIT ® L 30 D-55 (dry polymer) | 10-30% | 15-25% |
| Glycerol monostearate 40-55 | 4-8% | 5-7% |
| Triethyl citrate | 4-8 | 5-6% |
| Polysorbate 80 (Tween ® 80) | 6-10% | 7-9% |

TABLE 4b pH-responsive polymer composition and coating conditions

| Batch number | Batch size | Total polymer application | Ratio EUDRAGIT ® FS 30 D EUDRAGIT ® L 30 D-55 | Coating method |
|---|---|---|---|---|
| # 14 | 1000 | 3.5 mg/cm² 0.5 mg/cm² PEG 6000 | 62-66% EUDRAGIT ® FS 30 D 15-16% EUDRAGIT ® L 30 D-55 | Drum |
| # 02/04 | 3000 | 5.5 mg/cm² 0.5 mg/cm² PEG 6000 | 62-66% EUDRAGIT ® FS 30 D 15-16% EUDRAGIT ® L 30 D-55 | Fluid Bed |

TABLE 4b-continued pH-responsive polymer composition and coating conditions

| Batch number | Batch size | Total polymer application | Ratio EUDRAGIT® FS 30 D EUDRAGIT® L 30 D-55 | Coating method |
|---|---|---|---|---|
| # 06/08 | 3000 | 5.5 mg/cm² 0.5 mg/cm² PEG 6000 | 54-58% EUDRAGIT® FS 30 D 22-25% EUDRAGIT® L 30 D-55 | Fluid Bed |
| # 10/12 | 10,000 | 5.5 mg/cm² 0.5 mg/cm² PEG 6000 | 62-66% EUDRAGIT® FS 30 D 15-16% EUDRAGIT® L 30 D-55 | Fluid Bed |
| # 20A | 3000 | 4.0 mg/cm² | 62-66% EUDRAGIT® FS 30 D 15-16% EUDRAGIT® L 30 D-55 | Drum |
| # 20B | 3000 | 4.5 mg/cm² 0.5 mg/cm² PEG 6000 | 62-66% EUDRAGIT® FS 30 D 15-16% EUDRAGIT® L 30 D-55 | Drum |

The components are mixed together and the polymer is filtered (250 μm). For these batches, fluid bed and drum coating methods are used.

For fluid bed coating, the same conditions are used as those described for Example 2. In Example 4, Batch #14 (1,000 capsules) was produced using a medium sized coating drum (30 cm diameter) and applying 3.5 mg/cm² of polymer. For Batch #20B, 3,000 capsules were produced using the same equipment but a larger drum (36 cm diameter) and applying 4.5 mg/cm² polymer. The conditions are given below for the spraying phase:

|  | 30 cm drum | 36 cm drum |
|---|---|---|
| Inlet air volume m³/h: | 59 to 61 | 79 to 87 |
| Air flow temperature ° C.: | 30 to 40 | 32 to 38 |
| Product bed temperature ° C.: | 26 to 30 | 26 to 30 |
| Spraying velocity/min: | 1 to 3.5 | 2.5 to 6.5 |
| Polymer applied mg/cm² | 3.5 to 6.0 | 3.5 to 6.0 |

EXAMPLE 5

Dissolution Tests on Caffeine Filled Capsules of Example 4

The dissolution profiles of coated hypromellose capsules according to Example 4 that were filled with caffeine were determined. The tests were carried out in the same manner as those of Example 3. The results are shown in FIG. 2 and in Table 5 below.

No significant (<1%) dissolution is observed at pH 1.2 and 6.8. The release starts rapidly at pH 7.2. The results are shown in FIG. 2. Batch #14 corresponds to a capsule coated with 3.5 mg/cm² of polymer, while corresponds to a capsule coated with 5.5 mg/cm². Both are coated using drum coating. We note that Batch #20B releases its content slightly later (approximately 30 minutes later) than batch #14. Both batches (as well as all batches tested) have suitable dissolution profiles for use in FMT.

TABLE 5

Results of dissolution profile according to USP 2 method for capsules according to Example 5

| | | 20517/02-04 | | 20517/06-08 | | 20517/10-12 | | 20517/14 | | 20517/20B | |
|---|---|---|---|---|---|---|---|---|---|---|---|
| Medium | Time | Mean | SD | Mean | SD | Mean | SD | Mean | SD | Mean | SD |
| pH 1.2 | 0 | 0.00 | 0.02 | 0.00 | 0.01 | 0.01 | 0.02 | 0.00 | 0.02 | 0.00 | 0.00 |
| pH 1.2 | 60 | 0.02 | 0.03 | 0.00 | 0.01 | 0.01 | 0.02 | 0.01 | 0.03 | 0.01 | 0.01 |
| pH 1.2 | 120 | 0.01 | 0.01 | 0.01 | 0.01 | 0.03 | 0.02 | 0.03 | 0.03 | 0.00 | 0.03 |
| pH 6.8 | 150 | 0.06 | 0.06 | 0.35 | 0.15 | 0.05 | 0.05 | 0.79 | 0.19 | 0.18 | 0.12 |
| pH 6.8 | 180 | 0.76 | 0.37 | 4.16 | 2.92 | 1.18 | 0.40 | 4.65 | 1.87 | 1.35 | 0.34 |
| pH 7.2 | 190 | 1.50 | 0.61 | 7.88 | 6.34 | 2.85 | 1.23 | 8.95 | 4.32 | 2.24 | 0.54 |
| pH 7.2 | 200 | 3.14 | 0.94 | 22.95 | 27.81 | 6.77 | 2.24 | 35.39 | 33.09 | 3.64 | 1.62 |
| pH 7.2 | 210 | 7.04 | 3.27 | 28.86 | 30.13 | 13.53 | 5.13 | 57.12 | 37.15 | 5.60 | 2.93 |
| pH 7.2 | 225 | 18.78 | 9.30 | 43.23 | 29.38 | 37.19 | 17.89 | 80.03 | 20.17 | 29.49 | 4.02 |
| pH 7.2 | 240 | 49.29 | 36.35 | 60.53 | 26.45 | 63.62 | 19.06 | 95.03 | 4.93 | 59.75 | 5.28 |
| pH 7.2 | 300 | 96.70 | 3.05 | 99.24 | 0.54 | 99.56 | 0.79 | 99.33 | 0.23 | 100.24 | 0.06 |
| Homogenizate | 303 | 100.00 | 0.00 | 100.00 | 0.00 | 100.00 | 0.00 | 100.00 | 0.00 | 100.00 | 0.00 |

The invention claimed is:

1. A pharmaceutical oral formulation comprising a mixture of at least two bacteria derived from fecal microbiota encapsulated in a capsule, wherein the capsule is coated in a pH responsive polymer composition comprising:
   a. 50-70% poly(methyl acrylate-co-methyl methacrylate-co-methacrylic acid) 7:3:1 by weight of dry polymer,
   b. 10-30% poly(methacrylic acid-co-ethyl acrylate) 1:1 by weight of dry polymer,
   c. 5 to 10% by weight of at least one fatty acid mono-, di- or tri- glyceride ester, or mixtures thereof,
   d. 5 to 8% by weight of at least one plasticizer, and
   e. 6 to 9% by weight of at least one non-ionic emulsifier.

2. A pharmaceutical oral formulation of claim 1, wherein the capsule is coated in a pH responsive polymer composition comprising:
   a. 60-70% poly(methyl acrylate-co-methyl methacrylate-co-methacrylic acid) 7:3:1 by weight of dry polymer,
   b. 10-20% poly(methacrylic acid-co-ethyl acrylate) 1:1 by weight of dry polymer,
   c. 5 to 10% by weight of at least one fatty acid mono-, di- or tri- glyceride ester, or mixtures thereof, d. 5 to 8% by weight of at least one plasticizer, and
e. 6 to 9% by weight of at least one non-ionic emulsifier.

3. The pharmaceutical oral formulation of claim 1, wherein the capsule is made from hydroxypropyl methyl cellulose.

4. The pharmaceutical oral formulation of claim 1, wherein the pH responsive polymer composition comprises:
   a. 50-70% A poly(methyl acrylate-co-methyl methacrylate-co-methacrylic acid) 7:3:1 by weight of dry polymer,
   b. 10-30% A poly(methacrylic acid-co-ethyl acrylate) 1:1 by weight of dry polymer,
   c. 5 to 10% A by weight of glycerol monostearate,
   d. 5 to 8% by weight of triethyl citrate, and
   e. 6 to 9% by weight of at least one non-ionic emulsifier.

5. The pharmaceutical oral formulation of claim 1, wherein the pH responsive polymer composition comprises:
   a. 60-70% poly(methyl acrylate-co-methyl methacrylate-co-methacrylic acid) 7:3:1 by weight of dry polymer,
   b. 10-20% poly(methacrylic acid-co-ethyl acrylate) 1:1 by weight of dry polymer,
   c. 5 to 10% by weight of glycerol monostearate,
   d. 5 to 8% by weight of triethyl citrate, and
   e. 6 to 9% by weight of at least one non-ionic emulsifier.

6. The pharmaceutical oral formulation of claim 5, wherein the pH responsive polymer composition comprises:
   a. 62 to 66% poly(methyl acrylate-co-methyl methacrylate-co-methacrylic acid) 7:3:1 by weight of dry polymer,
   b. 14 to 18% poly(methacrylic acid-co-ethyl acrylate) 1:1 by weight of dry polymer,
   c. 5 to 8% by weight of glycerol monostearate,
   d. 5 to 8% by weight of triethyl citrate, and
   e. 6 to 9% by weight of polysorbate 80.

7. The pharmaceutical oral formulation of claim 1, wherein the encapsulated mixture of at least two bacteria derived from fecal microbiota comprises the entire fecal microbiota from one or more donors.

8. The pharmaceutical oral formulation of claim 1, wherein the mixture is present in the form of a lyophilizate.

9. The pharmaceutical oral formulation of claim 8, wherein the lyophilizate is produced by a method comprising:
   A) mixing a sample of fecal derived microbiota with a diluent comprising a polyol, a di-, tri- or polysaccharide or mixtures thereof and a filling agent, in a ratio of between 1:1 and 1:10, and
   B) freezing the mixture obtained in A) and then lyophilizing it.

10. The pharmaceutical oral formulation of claim 1, wherein the formulation comprises a mixture of at least two, or three, or four, or five, or six, or seven, or eight, or nine or ten bacteria derived from fecal microbiota.

11. The pharmaceutical oral formulation of claim 1, wherein the formulation comprises an entire fecal microbiota or a modified fecal microbiota.

12. A method for autologous or allogenic fecal microbiota transplantation, or for autologous or allogenic modified fecal microbiota transplantation in a subject in need thereof, comprising administering a therapeutically effective amount of the pharmaceutical oral formulation of claim 1 to the subject.

13. A method for treatment of gut dysbiosis and/or associated pathologies in a subject in need therof, comprising administering a therapeutically effective amount of the pharmaceutical oral formulation of claim 1 to the subject.

14. A method for the treatment of Iatrogenic gut dysbiosis and/or associated pathologies and/or complications in a subject in need thereof, comprising administering a therapeutically effective amount of the pharmaceutical oral formulation of claim 1 to the subject.

15. The method of claim 13, wherein the associated pathologies are Clostridium difficile infection and associated diarrhea (CDI), inflammatory bowel disease (IBD), irritable bowel syndrome (IBS), idiopathic constipation, celiac, disease, Crohn's disease, type II diabetes, food allergies, cancer, leukemia, refractory Graft-versus-host disease, obesity and morbid obesity, autism, sclerosis, traveler's diarrhea, chronic vaginal infection, bone and joint infections, Parkinson's disease, Alzheimer's disease, schizophrenia, and bipolar disorders and/or gut dysbiosis associated with anti-cancer chemotherapy or immunotherapy.

16. The method of claim 15, wherein the associated pathology is Inflammatory Bowel Disease (IBD), and wherein the bacteria in the formulation comprise a mixture of *Faecalibacterium prausnitzii Bacteroides fragilis, Roseburia intestinalis* and *Roseburia hominis*.

17. The method of claim 15, wherein the associated pathologies are obesity and diabetes, and wherein the bacteria in the formulation comprise a mixture of *Akkerrnansia muciniphila* and *Christensenella spp*.

18. The method of claim 15, wherein the associated pathology is gut bacteria in the formulation corn rise a mixture of Akkermansia muciniophila, Enterococcus s and *Bacteroides fragilis*.

19. The pharmaceutical oral formulation of claim 4, wherein the at least one non-ionic emulsifier has an HLB between 12 and 16.

20. The method of claim 14, wherein the associated pathologies and/or complications are sepsis, septic shock and/or gastro-intestinal disorders.

* * * * *